United States Patent
Ailhas et al.

(10) Patent No.: US 10,258,692 B2
(45) Date of Patent: Apr. 16, 2019

(54) ORAL PHARMACEUTICAL FORMULATION OF BCS CLASS III MOLECULES

(71) Applicant: ETHYPHARM, Saint-Cloud (FR)

(72) Inventors: Caroline Ailhas, Alizay (FR); Catherine Herry, Saint-Ouen du Tilleul (FR)

(73) Assignee: ETHYPHARM, Saint-Cloud (FR)

( * ) Notice: Subject to any disclaimer, the term of this patent is extended or adjusted under 35 U.S.C. 154(b) by 0 days.

(21) Appl. No.: 14/407,858

(22) PCT Filed: Jun. 14, 2013

(86) PCT No.: PCT/EP2013/062398
§ 371 (c)(1),
(2) Date: Feb. 27, 2015

(87) PCT Pub. No.: WO2013/186370
PCT Pub. Date: Dec. 19, 2013

(65) Prior Publication Data
US 2015/0165032 A1    Jun. 18, 2015

(30) Foreign Application Priority Data

Jun. 14, 2012 (FR) ..................... 12 55593

(51) Int. Cl.
| | | |
|---|---|---|
| *A61K 47/14* | (2017.01) | |
| *A61K 9/00* | (2006.01) | |
| *A61K 9/107* | (2006.01) | |
| *A61K 9/16* | (2006.01) | |
| *A61K 31/197* | (2006.01) | |
| *A61K 9/20* | (2006.01) | |
| *A61K 9/48* | (2006.01) | |
| *A61K 47/10* | (2017.01) | |
| *A61K 47/12* | (2006.01) | |

(52) U.S. Cl.
CPC ............ *A61K 47/14* (2013.01); *A61K 9/0095* (2013.01); *A61K 9/1075* (2013.01); *A61K 9/1617* (2013.01); *A61K 9/2013* (2013.01); *A61K 9/48* (2013.01); *A61K 31/197* (2013.01); *A61K 47/10* (2013.01); *A61K 47/12* (2013.01)

(58) Field of Classification Search
None
See application file for complete search history.

(56) References Cited

U.S. PATENT DOCUMENTS

| 2005/0191343 A1* | 9/2005 | Liang ........................... 424/450 |
| 2010/0029771 A1 | 2/2010 | Ameisen |
| 2010/0331356 A1* | 12/2010 | Legen et al. ................. 514/291 |

FOREIGN PATENT DOCUMENTS

| EP | 1 254 659 A1 | 11/2002 |
| WO | WO 2005/025559 A1 | 3/2005 |

OTHER PUBLICATIONS

International Search Report in PCT/EP2013/062398 dated Dec. 7, 2013.

\* cited by examiner

*Primary Examiner* — Hasan S Ahmed
(74) *Attorney, Agent, or Firm* — Dinsmore & Shohl LLP

(57) ABSTRACT

The present invention concerns an oral pharmaceutical formulation made from a microemulsion between an aqueous solution comprising at least one BCS (Biopharmaceutics Classification System) class III active principle and one oily phase comprising an oily vehicle that is self-emulsifiable on contact with water.

5 Claims, 8 Drawing Sheets

ORAL PHARMACEUTICAL FORMULATION OF BCS CLASS III MOLECULES

The invention concerns an oral pharmaceutical formulation of a BCS class III molecule such as baclofen having improved bioavailability and permeability.

The oral route is the first envisaged route when developing a novel pharmaceutical entity since it is conducive to promoting treatment compliance. However, this route is being abandoned for numerous molecules under development on account of their low oral bioavailability. This may be due to various factors related to the very properties of the molecules or to the physiology of the gastrointestinal tract (Fasinu, et al., 2011). Various approaches have been investigated over the last ten years to improve the oral bioavailability of these molecules including physical or chemical means.

DETAILED DESCRIPTION

The BCS classification of molecules (Biopharmaceutics Classification System) is a significant tool used for the development of oral forms in the pharmaceutical industry and has been adopted in particular by the FDA, EMEA and WHO (Dahan, et al., 2009). This system is divided into four categories of molecules and is based on the fundamental elements which control oral absorption i.e. intestinal membrane permeability and the solubility of a molecule in the gastrointestinal medium. A molecule is considered soluble if the maximum dose of an immediate-release form is soluble in 250 ml or less of an aqueous medium having a pH of between 1.2 and 6.8, and is considered permeable if its absorption through the intestinal membrane is 90% or higher. A BCS molecule belonging to class III is highly soluble and scarcely permeable. This latter characteristic is the factor limiting oral bioavailability and may lead to abandoning the development of an oral formulation of molecules nevertheless having strong therapeutic potential.

Figure 1:
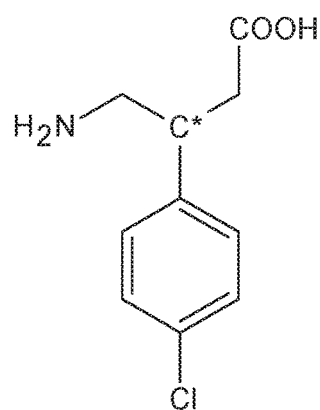
FIG. 1 is a graphical depiction of the baclofen formula.

Baclofen (FIG. 1) is a BCS class III molecule. Its physicochemical characteristics are summarized in Table 1.

TABLE 1

PHYSICOCHEMICAL CHARACTERISTICS
OF BACLOFEN (INTERNAL REPORT)

| | |
|---|---|
| Molar mass | 213.66 g/mol |
| Melting point | 180-191° C. |
| pH of a saturated solution | 6.5 |
| pKa | $pKa_1 = 3.87$ |
| | $pKa_2 = 9.62$ |
| Solubility | Soluble: 0.1N HCl, 0.1N NaOH |
| | Slightly soluble: water (3 mg/ml) |
| | Very slightly soluble: Ethanol, Methanol |
| Log P | −1 |

At usual therapeutic doses, baclofen is known to have good oral bioavailability. Yet its low log P indicates some hydrophilicity and hence low permeability. This observation can be accounted for by the presence of specific transporters at the small intestine allowing the molecule to pass. The transport of the molecule is greater at the jejunum. Therefore low transport at the colon would indicate the presence of another transport mechanism through the intestinal barrier (Merino, et al., 1989). This region of the digestive system does not contain any transporters but since the molecule is hydrophilic and of small size, some passive transport through the tight junctions is possible. It therefore appears that when a higher plasma concentration of baclofen is desired, the taking of a higher dose is not efficient on account of saturation of the transporters. The clinical solution applied is to take smaller doses at closer time intervals which may soon become burdensome for the patient.

An increase in the lipophilicity of baclofen and thereby its transcellular permeability was observed when producing prodrugs of baclofen ester (Leisen, et al., 2003). Through these properties a greater concentration of prodrug was found at the target tissue i.e. the brain due to easier crossing of the blood brain barrier. However, greater affinity for the efflux pump P-gp is to be noted as well as partial hydrolysis of the prodrug to baclofen which finally leads to a lower level of baclofen at the site of action after administration of the prodrug compared with administration of baclofen alone.

A baclofen absorption window was evidenced at the small intestine due to the presence of transporters (Merino, et al., 1989). To increase bioavailability, this absorption window could be used to advantage for pharmaceutical techniques allowing the retaining of the oral form at or upstream of the window (Davis, 2005). A longer residence time at the absorption site should theoretically allow more extensive movement of molecules across the intestinal barrier if they are not likely to undergo pre-systemic degradation before being absorbed. Therefore, bioadhesive forms adhering to the intestinal mucus through the use of cationic polymers such as chitosan, or gastro-retaining forms allowing the swelling and floating of the form in the stomach have been developed in recent years in the pharmaceutical sector but their efficacy is highly dependent on intra- and interindividual variability.

Figure 2:
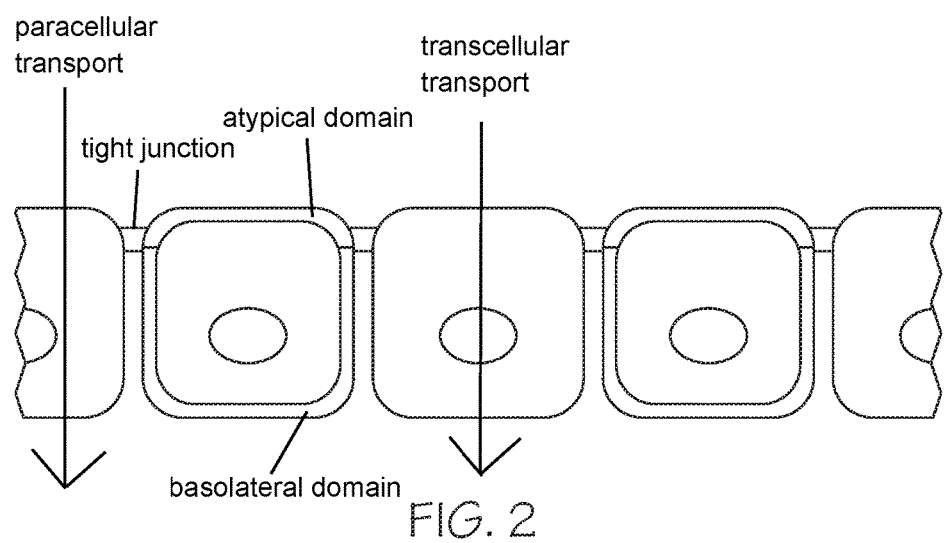
FIGS. 2 and 3 are schematic representations of the tight junctions described herein.
Figure 3:
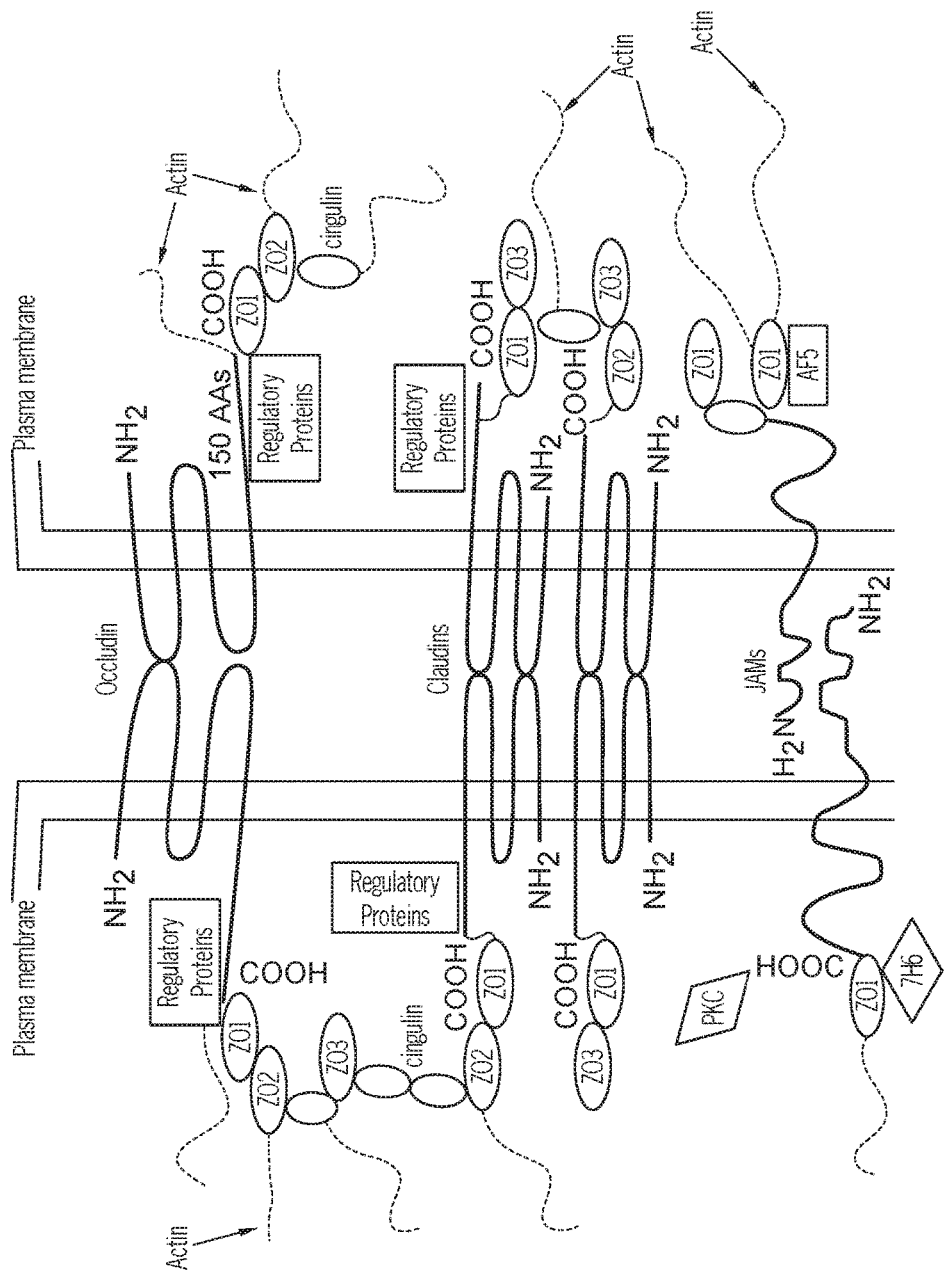

Under normal physiological conditions, the paracellular pathway takes up less than 0.1% of the total surface area of the intestinal epithelium, and it is therefore not a major pathway (Anilkumar, et al., 2001). This can be attributed to the presence of tight junctions between the cells which limits the absorption of molecules of size greater than 0.1 nm. Therefore action on the latter could allow a significant increase in absorption. The tight junctions play a barrier role between the components of the apical and basolateral domains, and are composed of various protein complexes involved in the regulation of the integrity of the junctions (zonula occludens, actin, claudin-1, . . . ) (FIGS. 2 and 3). This integrity is modified by confrontation with various physiological and pathological agents and in particular by secondary messengers originating from the signalling pathways. Two factors appear to be involved in the face of action by absorption enhancers: the contraction an actin-myosin ring and phosphorylation by kinase and phosphatase proteins. Anilkumar et al. listed the absorption enhancers that are the subject of research for this indication. These include surfactants, biliary acids and derivatives, fatty acids and derivatives, chelating agents, chitosan and the derivatives thereof, and the polycarbophylcysteine conjugate.

Therefore, since the tight junctions have a barrier role and hence a defensive role in the body, it is important that the enhancers acting on the opening thereof should have reversible action not inducing any toxicity.

Surprisingly, the inventors have discovered that the bioavailability and more particularly the intestinal membrane permeability of BCS class III molecules can be considerably improved by the formulation thereof in the form of an oil-in-water microemulsion, the BCS class III molecule being aqueous and the oil phase being formed of an oil excipient that is self-emulsifiable in contact with water.

In particular, they have observed an increase in baclofen permeability on Caco-2 cells when it is in an oil-in-water microemulsion formulation between an aqueous solution of baclofen at 6 mg/mL in 0.01 M fumaric acid and Labrasol®.

Consequently, the subject of the invention concerns an oral pharmaceutical formulation containing a microemulsion between an aqueous phase comprising at least one BCS (Biopharmaceutics Classification System) class III active ingredient and an oil phase comprising an oil excipient self-emulsifiable in contact with water.

The formulation of the invention has the advantages of improved intestinal membrane permeability and non-toxicity.

By microemulsion is meant an emulsion having a droplet size of less than 200 µm.

By "oil excipient self-emulsifiable in contact with water" is meant an excipient which will spontaneously form an oil-in-water emulsion with an aqueous phase i.e. droplets of the aqueous phase surrounded by a lipid layer containing the excipient.

To assess the potential of an absorption enhancer to increase permeability, in vivo techniques in the rat or ex-vivo techniques (on infused rat intestine) can be carried out (Koga, et al., 2002) (Lin, et al., 2007) (Constantinides, et al., 1996). In vitro techniques are also used on rat intestinal membrane or cell cultures. As first approach, evaluation on the Caco-2 cell line is very often applied (Sha, et al., 2005).

The Caco-2 cells are derived from the culture of human cells of cancerous origin capable of differentiating in the presence of a suitable culture medium (Pontier, 1997-1998). Their properties are a function of the number of subcultures to which they are subjected. The clone of cells obtained at passage 198 shows characteristics close to those of enterocytes. The size of Caco-2 cells is slightly smaller than that of healthy enterocytes but they have a monolayer comparable to that of the epithelium of the small intestine. The brush-border is differentiated and developed with very tight junctions of 10 to 50 Å (narrower than those of the small intestine). From a biochemical viewpoint, Caco-2 cells also express the enzymes of the enterocytes. In addition, numerous transporters are present but their expression is lower than the levels found in vivo and the P-gp efflux pump is over-expressed which may underestimate absorption compared with in vivo.

The MTT assay is an indicator of mitochondrial integrity and activity and can be likened to measurement of cell viability (Sigentec). This assay is based on the activity of a mitochondrial enzyme, succinate dehydrogenase. In the presence of the MTT substrate (3-[4,5-dimethylthiazol-2yl]-2,5-diphenyltetrazolium bromide), the tetrazolium salts of the substrate are converted to insoluble crystals of formazan through the activity of the succinate dehydrogenase. After solubilisation, the quantity of formazan salt is assayed by spectrophotometry and compared with a negative control having a cell viability of 100% (Buyukorturk, et al., 2010).

Measurement of transepithelial electrical resistance (TEER) (in ohms/cm$^2$) allows evaluation of cell integrity (Pontier, 1997-1998). This allows evaluation of the toxicity of the assayed product. Measurement is performed before and after the assay and loss of resistance must not exceed 30% for a conclusion of non-toxicity (Oroxcell, 2011).

Lucifer yellow (LY) is a marker of paracellular transport (Buyukorturk, et al., 2010). Its measurement in the receiver compartment during the permeability assay allows observation of the opening of the tight junctions. Measurement can also be performed after the assay to evaluate cell integrity (Nollevaux, et al., 2006). The apparent permeability of Lucifer Yellow under normal conditions is $3·10^7$ cm/s (Oroxcell, 2011).

Preferably the ratio by weight of BCS class III active ingredient/oil excipient self emulsifiable in contact with water is between 1:10 and 1:100, more preferably between 1:40 and 1:80.

Preferably the oil phase represents 1 to 50% of the microemulsion, more preferably 2 to 30%, further preferably 5 to 25%, and still further preferably 15 to 20%.

Preferably, the aqueous phase of the microemulsion of the formulation of the invention is a solution in which the BCS class III active ingredient is solubilised.

Preferably, the microemulsion of the formulation of the invention is an oil-in-water microemulsion formed of an aqueous phase comprising at least one BCS (Biopharmaceutics Classification System) class III active ingredient and an oil excipient self-emulsifiable in contact with water.

Preferably, the active ingredient of the formulation of the invention is selected from among the following BCS class III molecules: ranitidine, cimetidine, atenolol, vancomycin, baclofen, fexofenadine, calcitonin, calcein, the bisphosphonates, peptides such as octreotide, lanreotide, leuprorelin, insulin and the analogues or agonist of GLP-1 (glucagon-like peptide-1).

The particularly preferred active ingredient of the formulation of the invention is baclofen. According to one preferred embodiment it is solubilised in the aqueous phase, preferably in 0.01 M fumaric acid.

Preferably, a suitable oil excipient self-emulsifiable in contact with water has an HLB number (Hydrophilic-Lipophilic Balance) higher than 12, more preferably 13 or 14, for example it is Labrasol® (Gattefossé) composed of caprylo-caproylmacrogolglycerides, or semi-solid Gélucire 50/13® composed of lauroylmacrogolglycerides (Gattefossé).

A particularly preferred suitable oil excipient self-emulsifiable in contact with water is selected from the group formed by:
    C8 to C10 fatty acids, whether or not pegylated such as sodium caprate or one of the derivatives thereof;

C8C10 triglycerides, such as the triglycerides of capric (C10) and caprylic (C8) acid, for example Miglyol and Captex® (Sasol Germany GmbH, 2012), mixtures of mono-, bi- and triglycerides, such as Capmul® (Abitec, 2012), mixtures of mono-, bi- and triglycerides of esterified fatty acids of propylene glycol, e.g. capric and caprylic acids such as caprylocaproylmacrogolglycerides or a mixture of mono-, bi- and triglycerides of PEG-8 esterified fatty acids in a proportion of 50 to 80% caprylic acid and 20 to 50% capric acid e.g. Labrasol®.

The Miglyol® (Sasol) and Captex® (Abitec) products are triglycerides of capric acid (C10) and caprylic acid (C8).

ides composed of a mixture of mono-, bi- and triglycerides of esterified fatty acids of propylene glycol-8, in a proportion of 50 to 80% caprylic acid and 20 to 50% capric acid. A further subject of the invention concerns a formulation of the invention for use thereof in the treatment of alcohol dependence or for maintaining alcohol abstinence.

A further subject of the invention concerns the use of a microemulsion between an aqueous phase comprising at least one BCS (Biopharmaceutics Classification System) class III active ingredient and an oil phase comprising an oil excipient self-emulsifiable in contact with water to produce a medicinal product intended for the treatment of alcohol dependence or for the maintaining of alcohol abstinence.

TABLE 2

CHARACTERISTICS OF COMMERCIAL FATTY ACID DERIVATIVES (ABITEC, 2012)(GATTEFOSSE)(SASOL GERMANY GMBH, 2012)

| | Miglyol® 810 | Miglyol® 812 | Miglyol® 829 | Captex® 300 EP/NF | Captex® 355 EP/NF | Captex® 200P | Capmul® MCM, EP | Labrasol® | Gelucire® 50/13 |
|---|---|---|---|---|---|---|---|---|---|
| Composition | Triglycerides of: 65-80% caprylic acid (C8:0)/ 20-35% capric acid (C10:0) | Triglycerides of: 50-65% caprylic acid/ 30-45% capric acid | Triglycerides of: 45-65% caprylic acid/30-45% capric acid/ 15-20% succinic acid | Triglycerides of: 50-80% caprylic acid/ 20-50% capric acid | Triglycerides of: 50-80% caprylic acid/ 20-50% capric acid | Propylene glycol of: 50-80% caprylic acid/ 20-50% capric acid | 50-90% caprylic acid/ 10-50% capric acid/ 45-75% mono; 20-50% di; 10% triacyl-glycerols | Triglycerides and mono/ di PEG-8 esters of: 50-80% caprylic acid/20-50% capric acid | 40-50% palmitic acid (C16)/ 48-58% stearic acid (C18) |
| Physical state at $T_{amb}$ | Liquid | Liquid | Liquid | Liquid | Liquid | Liquid | Semi-solid | Liquid | Semi-solid m.p. = 50° C. |
| Solubility | Hexane, toluene-diethylether, ethylacetate, acetone, isopropanol, 96% ethanol | Hexane, toluene-diethylether, ethylacetate, acetone, isopropanol, 96% ethanol | Hexane, toluene-diethylether, ethylacetate, acetone, isopropanol, 96% ethanol | Organic solvents incl. 95% ethanol | Organic solvents incl. 95% ethanol | unkn. | unkn. | Ethanol 96°: very soluble Chloroform, methylene chloride: very soluble Water: soluble (HLB = 14) Mineral oils: insoluble | Ethanol 96°: insoluble Chloroform: easily soluble Methylene chloride: easily soluble Water: dispersible (HLB = 13) Mineral oils: insoluble |
| Refractive index | 1.448-1.451 | 1.449-1.451 | 1.456-1.459 | 1.440-1.452 | 1.440-1.452 | unkn. | unkn. | 1.450-1.470 | unkn. |
| Density at 20° C. (g/cm³) | 0.94-0.95 | 0.94-0.95 | 1.00-1.02 | 0.93-0.96 | 0.93-0.96 | unkn. | unkn. | 1.060-1.070 | unkn. |
| Viscosity at 20° C. (mPa · s) | 27-33 | 27-33 | 230-270 | 25-33 | 25-33 | unkn. | unkn. | 80-110 | unkn. |
| Regulatory status | EP, USP, BP, GRAS | EP, USP, BP, GRAS | DMF, GRAS | EP/NF, DMF | EP/NF, DMF | EP/NF, USP, DMF | EP, DMF, GRAS | EP, USP/NF | EP, USP/NF |

UNKN. = UNKNOWN

Capmul® MCM (Abitec) is a compound of mono- and diglycerides of capric and caprylic acid (Table 2).

Labrasol® (Gattefossé) is composed of caprylocaproyl-macrogolglycerides, which is a mixture of mono-, bi- and triglycerides and of esterified fatty acids of propylene glycol (Gattefossé). Its characteristics (Table 2), and in particular its miscibility with water prove to be of particular interest from a formulation viewpoint.

Gélucire® 50/13 (Table 2) is a semisolid excipient of high HLB, having 13 compounds of Lauroylmacrogolglycerides (Gattefossé). Palmitic acid and stearic acid are the constituent fatty acids of Gélucire®.

The particularly preferred self-emulsifiable oil excipient of the microemulsion of the formulation of the invention is Labrasol®, i.e. a mixture of caprylocaproylmacrogolglycer- The pharmaceutical formulation of the invention may be any oral pharmaceutical formulation known to persons skilled in the art, whether liquid or solid.

Suitable liquid formations are any liquid pharmaceutical formulation wherein the microemulsion between an aqueous phase comprising at least one BCS class III active ingredient (Biopharmaceutics Classification System) and an oil phase comprising an oil excipient self-emulsifiable in contact with water will remain stable.

The microemulsions, once formed, can be directly placed in soft or hard capsules e.g. in gelatine for oral administration.

Numerous techniques are known to formulate a solid form from a liquid formula (Jannin, et al., 2008). Spraying in a cold chamber for example can be used to freeze droplets which recrystallize in the form of solid spherical particles.

The aqueous phase of an emulsion can also be spray dried in a fluidised air bed to form a "dry emulsion".

It can also be sprayed onto neutral beads optionally having adsorption capacities such as spheroids of microcrystalline cellulose. After drying, these spheroids can be used to formulate tablets with compression excipients.

The use of excipients solid at ambient temperature but liquid when hot allows application of thermogranulation or extrusion-spheronization techniques.

Finally, adsorption on a solid carrier such as microcrystalline cellulose or silica, in a mixer-granulator, allows the adsorption of a large amount of liquid excipient whilst maintaining good flow properties. After drying, the carrier impregnated with emulsion can be used to formulate tablets with compression excipients.

The formulation of the invention may comprise any additional conventional excipient used in formulations.

The formulation of the invention comprises 10 to 80 mg active ingredient per unit dose, preferably 20 to 60.

EXAMPLES

Example 1: Materials and Methods a. Raw Materials
i. Active Ingredient
Baclofen was obtained from PCAS.
ii. Adsorption Enhancers
Labrasol® and Gélucire® 50/13 were supplied by Gattefossé®, Miglyol® 810 by Sasol® Germany GmBH and Capmul® MCM and Captex® 355 by Abitec®.
iii. Other Excipients
The excipients used for the different assays were the following: Fumaric acid (Merck), Avicel® PH102 (microcrystalline cellulose, FMC Biopolymer), Neusilin® (magnesium aluminometasilicate, FugiChemicalIndustry), HPMC 603 (hydroxypropylmethylcellulose, Shin Etsu), Tween® 80 (polysorbate 80, Sigma).
b. Baclofen Solubility Assays
Beforehand it is important to determine the solubility of the active ingredient in the excipients to be evaluated. For the purpose of cell assays, it is important that the active ingredient should be in molecular form to obtain crossmembrane transport. Solubility was determined via visual method by adding exactly weighed quantities of baclofen to the selected excipients, after being left under agitation for 24 h. First the solubility of baclofen at ambient temperature in Labrasol®, Miglyol® 810 and Captex® 355 was determined. The solubility of baclofen in Gélucire® 50/13 was determined after melting the excipient at a temperature higher than 50° C. and placing thereof in a thermostat-controlled oven at 60° C. At a second step, to increase the solubility of baclofen in an aqueous medium, this solubility was determined in an acidified solution of 0.01 M fumaric acid. According to an internal report on binary compatibilities, fumaric acid does not cause any stability problems with baclofen.
c. Lipid Formulations
i. Microemulsions
Miglyol® 810, Capmul® MCM and Captex® 355 are excipients non-miscible with water. Since baclofen is a hydrophilic molecule, it was chosen to formulate microemulsions from these excipients using pseudo-ternary diagrams. That is to say having a fixed surfactant/co-surfactant composition but varying the proportion of this mixture with the oil and water phases. The objective was to formulate an oil-in-water (O/W) microemulsion and water-in-oil (W/O) microemulsion.

Figure 4:
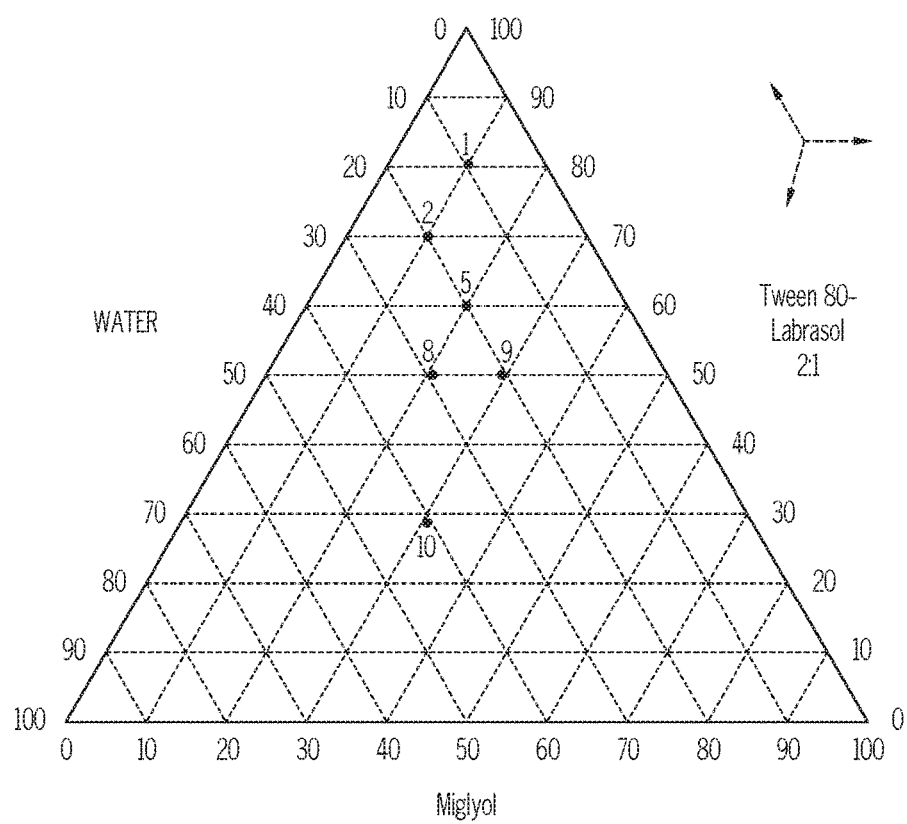
FIG. 4 depicts a composition of oil-in-water microemulsions produced from Miglyol® and Labrasol® in accordance with Example 1.

Six assays were carried out to obtain an O/W microemulsion using a surfactant-co-surfactant mixture of Tween®-80Labrasol® in 2:1 proportion and Miglyol® 810 for the oil phase (FIG. 4).

Figure 5:
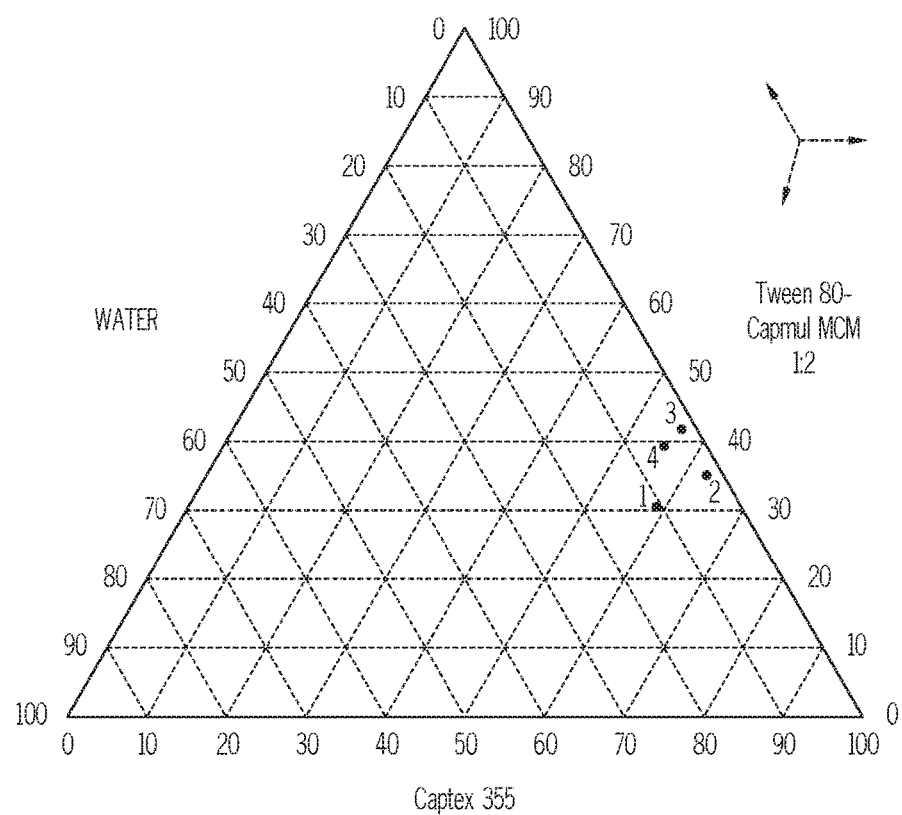
FIG. 5 depicts a composition of water-in-oil microemulsions produced from Captex® and Capmul® in accordance with Example 1.

Four assays were conducted to obtain a W/O microemulsion using a surfactant-co-surfactant mixture of Tween®-80Capmul® MCM in 1:2 proportion and Captex® 355 for the oil phase (FIG. 5).

The aqueous phase composed of purified water was added last under agitation. The microemulsions are formed instantly. Once the composition of the mixtures was selected, assays were performed with an aqueous solution of 0.01 M fumaric acid with 6 mg/ml of baclofen.

ii. Binary Mixtures

Labrasol® and Gélucire® 50/13 are excipients which self-emulsify in the presence of water. Various water/Labrasol® or water/Gélucire® 50/13 ratios were tested. The mixtures of water/Gélucire® 50/13 were formed at a temperature higher than 50° C. whilst the mixtures of water/Labrasol® were conducted at ambient temperature.

iii. Characterization

1. Viscosities

The viscosity of the emulsions was determined using a rotary Brookfield DV-II+ viscometer and SC4-18 spindle with cylindrical Couette geometry.

2. Particle Sizes

The particle size of the emulsions was measured by dynamic light scattering on Coulter® N4 plus particle analyzer. Measurements were taken at an angle of 90° directly on the emulsions taking into account the characteristics of the dispersing medium (viscosity, refractive index) then after dilution in water. The dilution factor is dependent upon the intensity measured at 90°, which must lie between $5 \cdot 10^4$ and $1 \cdot 10^6$ counts/sec for validation of the measurement. Each measurement was performed in triplicate.

3. Stabilities

The stability of the emulsions was determined visually over two months by observing the onset or non-onset of phase separation and by particle size measurement. The measurements obtained at time t=14 days and t=45 days were compared.

d. Selection of Formulas: Permeability Assays on Caco-2 Cells i. Cell Culture

The Caco-2 cells were placed in culture and differentiated over 21 to 30 days. They were subjected to a number of subcultures of less than 110. The culture medium was DMEM (Dulbecco's Modified Eagle Medium) supplemented with inactivated 10% foetal calf serum, with 1% non-essential amino acids and antibiotics.

ii. Permeability Assay

The Caco-2 cells allowed evaluation of the potential of eight formulas given in Tables 5a, 5b, 5c and 5d, for improvement in the apparent permeability of baclofen. The dilutions are those chosen by the subcontractor as a function of baclofen concentration measured by the assay technique and as a function of the lowest non-toxic concentration given by preliminary toxicity studies. The compositions of the apical and basolateral media are given in Table 3 below.

TABLE 3

Composition of the apical and basolateral media for assays on Caco-2 cells

| Apical medium | Basolateral medium |
|---|---|
| HBSS | HBSS |
| 10 mM HEPES | 10 mM HEPES |
| 0.1% BSA | 0.1% BSA |
| 200 µM Lucifer Yellow | — |
| pH 6.8 | pH 7.4 |

Samples were taken after the placing the test specimen in the apical medium: at T5 minutes and T125 minutes in the donor compartment and at T65 minutes and T125 minutes in the receiver compartment. The assay of baclofen was performed using LC/MS/MS analysis.

The apparent permeability of baclofen and the recovery ratio were calculated as follows:

$Papp=[\Delta Q/(\Delta t \times A)]/C_0$ where $Papp$=apparent permeability (cm·s$^{-1}$)

$\Delta Q$=difference in amount of baclofen measured between the two samplings $\Delta t$=time interval between the two samplings A=exposure surface area (cm$^2$)

$C_0$=initial concentration deposited in the donor compartment.

The result was interpreted as follows:

TABLE 4

Interpretation of apparent permeability results

| Permeability | Low | Medium | High |
|---|---|---|---|
| $P_{app} \times 10^{-6}$ cm/s | <0.5 | 0.5 to 5 | >5 |

TABLE 5a

Centesimal composition of oil-in-water microemulsion

| Ingredients | Percentage |
|---|---|
| Captex 355 | 60 |
| Capmul MCM | 20 |
| Tween 80 | 10 |
| Aqueous solution of baclofen | 10 |
| Total | 100 |

TABLE 5b

Centesimal composition of oil-in-water emulsion

| Ingredients | Percentage |
|---|---|
| Miglyol 810 | 20 |
| Labrasol | 20 |
| Tween 80 | 40 |
| Aqueous solution of baclofen | 20 |
| Total | 100 |

TABLE 5c

Centesimal composition of the emulsion of water-labrasol solution

| Ingredients | Percentage (25% labrasol solution) | Percentage (10% labrasol solution) | Percentage (5% labrasol solution) | Percentage (1% labrasol solution) |
|---|---|---|---|---|
| Labrasol | 25 | 10 | 5 | 1 |
| Aqueous solution of baclofen | 75 | 90 | 95 | 99 |
| Total | 100 | 100 | 100 | 100 |

TABLE 5d emulsion of the water-gélucire solution

| Ingredients | Percentage (5% gélucire solution) | Percentage (1% gélucire solution) |
|---|---|---|
| Gélucire 50/13 | 5 | 1 |
| Aqueous solution of baclofen | 95 | 99 |
| Total | 100 | 100 |

$$\text{Recovery} = \begin{bmatrix} \text{Residual} & & \text{Accumulated} \\ \text{amount in} & & \text{amount in receiver} \\ \text{donor} & + & \text{compartment} \\ \text{compartment} & & \text{between T5 and} \\ \text{at T125} & & \text{T125} \end{bmatrix} \Big/ \begin{matrix} \text{Amount at T5} \\ \text{in donor} \\ \text{compartment} \end{matrix}$$

The result should be between 75 and 125%.

Each assay was performed three times. For the validity of the assay, the permeability of a reference compound was also measured as positive control. This compound was 20 µM metoprolol, a molecule with active transcellular transport. Baclofen alone was also used as negative control.

iii. Evaluation of Cell Integrity

1. Measurement of Transepithelial Resistance

Before each assay transepithelial resistance was measured. This must be higher than 1500Ω. A second measurement was performed after the assay. If loss of resistance is higher than 30%, the monolayer is considered to be deteriorated.

2. Lucifer Yellow Test

Throughout the assays the crossing of Lucifer Yellow from the apical to the basolateral compartment, a marker of paracellular transport, was also evaluated. 200 µM of Lucifer Yellow was co-incubated with the test compound and its permeability evaluated in the same manner as for the latter. Concentrations were measured by fluorescence in both compartments at the start and at the end of the assay.

3. MTS-PMS Test

The MTS-PMS test is a derivative of the MTT test and allows verification of cell viability. The living cells convert MTS to formazan that is soluble in the culture medium. The amount of formazan produced is evaluated by measuring absorbency at 490 nm. This amount is directly related to the proportion of living cells in the medium.

e. Placing in Solid Form: Adsorption/Granulation Technique

Further to the results of the assays on cells, the excipient selected for the formulation of a solid form was Labrasol®. The adsorption/granulation assays were performed in a Diosna PVAC 10 mixer/granulator. A 2 L bowl and 0.8 mm spray nozzle were used.

i. Granulation Tests

Granulation tests were performed on microcrystalline cellulose (Avicel® PH102) as indicated in Table 6. The rotational speed of the bottom blade was 200 rpm and the speed of the chopper was 1500 rpm. The spray flow rate was 30 g/min. A drying time of one hour at 50° C. in vacuo was needed to obtain granulate containing residual moisture of less than 5% (Mettler thermobalance). The granules were then screened through 0.5 mm mesh size.

TABLE 6

Composition of granulation assay

| Dry load | Function of excipients | Formula (%) | Quantity (g) QS 300 g |
|---|---|---|---|
| Avicel ® pH 102 | Adsorbent | 95 | 285 |
| HPMC 603 | Binder | 5 | 15 |

| Wetting solution | — | Formula (%) | Quantity (g) QS 300 g |
|---|---|---|---|
| Purified water | Granulating agent | 50 | 150 |
| Labrasol ® | Absorption enhancer | 50 | 150 |

Particle size was measured with a Malvern® laser particle size analyzer and the data processed using Mastersizer 2000 software. The granulate compressibility and flow capabilities were evaluated by measurement of the tapped apparent volume (STAV 2003 volumeter, automatic tapper), calculation of the Carr index and by measuring the flow time of 100 g of powder through a standardized funnel. These tests were conducted in accordance with the European Pharmacopeia in force (*European Pharmacopeia 7<sup>the</sup> Edition*, 2012).

ii. Adsorption Assays

Simple adsorption assays were also performed in a mixer by adding Labrasol® to Avicel® PH102 or Neusilin® (Magnesiumaluminometasilicate) under impeller agitation of 150 and 300 rpm respectively. The flow rate was 20 g/min and assays were conducted under heat at 40° C. in vacua to fluidise the oil excipient: Labrasol. The following adsorbents were also tested: Fujicalin®, Hubersorb®, 600 and Syloïd®244FP.

Example 2: Results a. Solubility Values of Baclofen

The solubility values indicated in Table 7 below were determined in relation to visual observation of particles in the media.

TABLE 7

Results of baclofen solubility in various media

| Product | Temperature | Solubility of baclofen |
|---|---|---|
| Miglyol ® 810 | Ambient | <0.1 mg/ml |
| Captex ® 355 | Ambient | <0.1 mg/ml |
| Labrasol ® | Ambient | 0.2-0.4 mg/ml |
| Gélucire ® 50/13 | 60° C. | 0.5-1 mg/ml |
| 0.01M fumaric acid aqueous medium | Ambient | 6-7 mg/ml |

Baclofen appears to be soluble in an aqueous medium and practically insoluble in oil excipients.

b. Lipid Formulations i. Microemulsions

In relation to the compositions obtained various observations can be made. Regarding the microemulsions containing Miglyol® 810 and Labrasol® (FIGS. 4 and 5), compositions 1, 2 and 3 allow clear media to be obtained and composition 10 produces a milky medium. Compositions 8 and 9 are opaque with phase separation after 24 h.

The four compositions produced with Captex® 355 and Capmul® MCM give clear microemulsions.

The microemulsions produced with active ingredient did not exhibit any visual difference compared with those without active ingredient.

ii. Binary Mixtures

Labrasol® is miscible in any proportion in water. However a clear, homogenous mixture is obtained at Labrasol concentrations higher than 1% in water. At concentrations below 1% the medium becomes turbid and particles visible to the naked eye are seen to sediment.

Gélucire® is also miscible in water but only water/Gélucire® mixtures at concentrations below 5% remain in liquid form at ambient temperature.

iii. Characterization

In relation to the criteria discussed below, some compositions were retained for permeability assays on cells and are characterized herein.

1. Viscosities

The viscosities of the microemulsions are given in Table 8 below. The torque value gives an indication on the reliability of measurement.

TABLE 8

Viscosity of the microemulsions at ambient temperature

| Sample | Spindle rotation speed (rpm) | Torque value (%) | Measured viscosity (cP) |
|---|---|---|---|
| Microemulsion Miglyol ®/Labrasol ® | 6 | 85 | 423 |
| Microemulsion Capmul ®/Captex ® | 30 | 60 | 59 |

The viscosities of the binary mixtures are close to that of water.

2. Particle Sizes

Particle sizes were measured 14 days after preparation of the systems, before and after dilution for the microemulsions and for the binary water/Labrasol® mixtures. The results are given in Tables 9 and 10.

For the microemulsions, dilution causes destabilisation and the onset of an opaque medium having intensity at 90° that is too high for measurement of particle size. Dilution is needed to obtain intensity within the range recommended by the manufacturer of the particle size analyzer. The characteristics and in particular the viscosity of the nondiluted Miglyol®/Labrasol® emulsion do not allow measurements on the Coulter particle size analyzer.

For the water/Labrasol® mixtures, dilution was identical to that of the assays on Caco-2 cells.

3. Stability of the Microemulsions at T=45 Days

Particle size measurements given in Table 9 were also carried out and compared with those obtained at 14 days. No phase separation was observed for the microemulsions placed at ambient temperature after 45 days.

c. Permeability Assays on Caco-2 and Membrane Integrity

Figure 6:
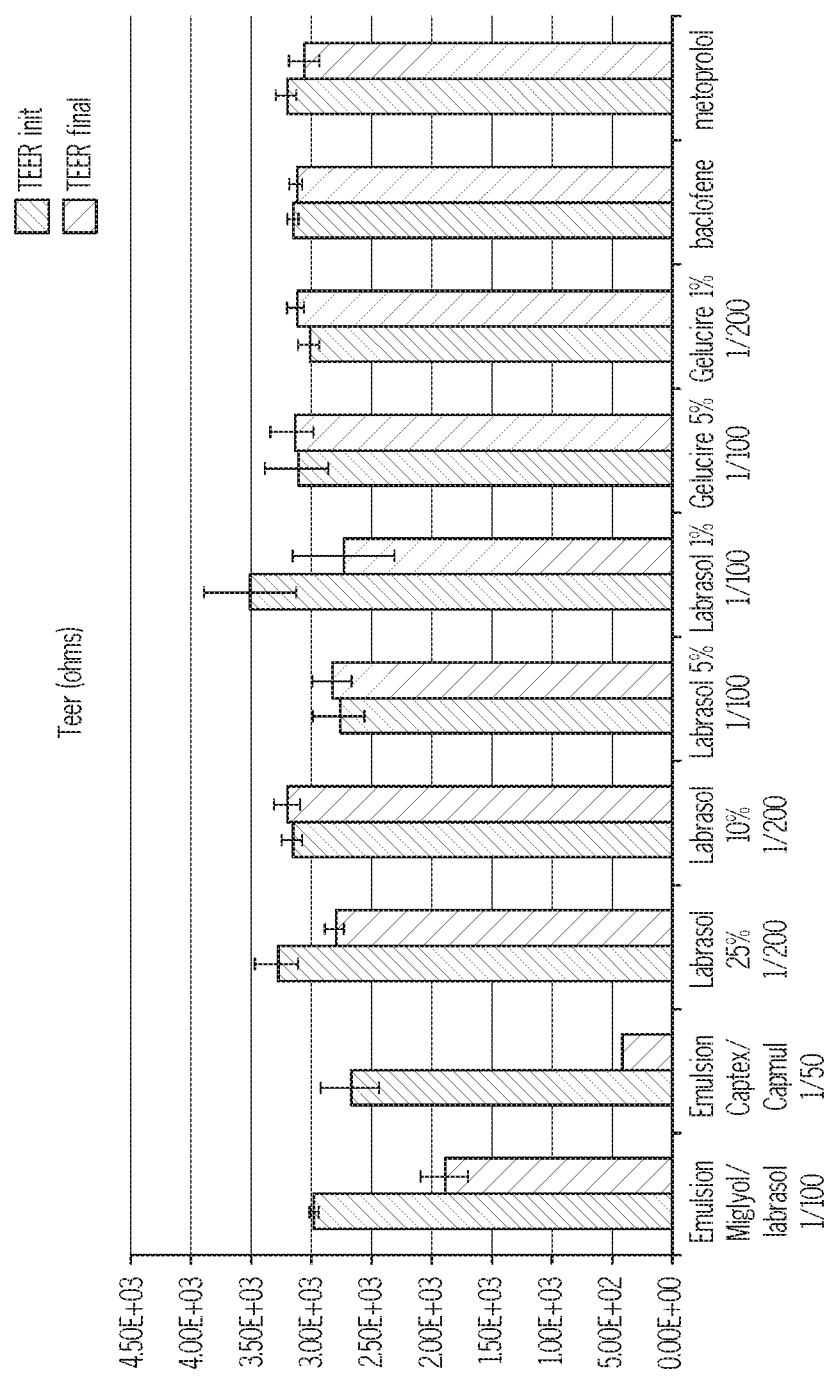
FIG. 6 is a graph depicting initial and final measurements of transepithelial resistance as a function assays on cells in accordance with Example 2.

Measurement of transepithelial resistance (FIG. 6) before and after the permeability assay gave information on the toxic potential of the eight formulas and of the different controls. Solely the microemulsions led to a variation in resistance higher than 30% between the initial and final measurements, indicating loss of membrane integrity. The 6 other formulas and the controls caused a variation lower than 30% indicating recovery of cell resistance after the assay. Membrane integrity is therefore not affected by these formulas.

Figure 7:
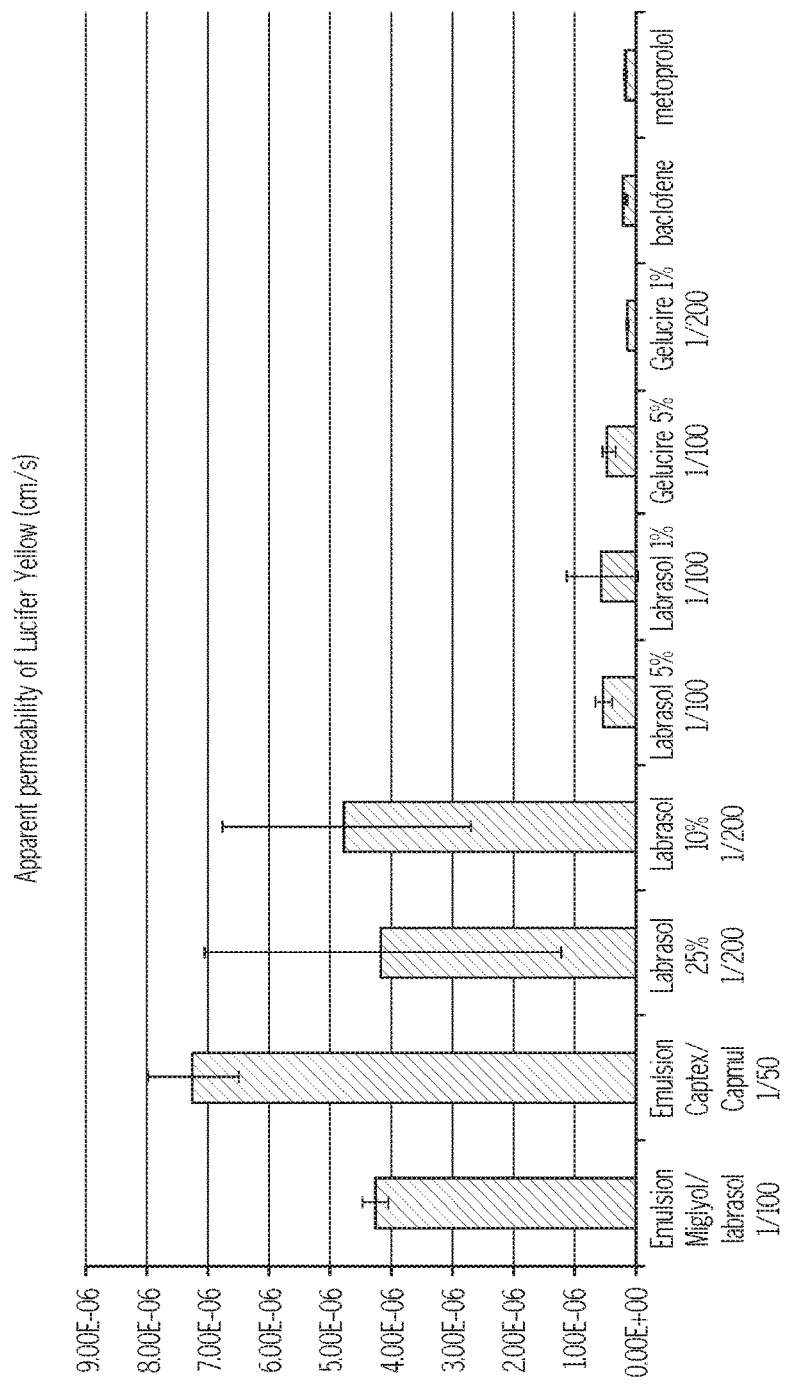
FIG. 7 is a graph depicting apparent permeability of *Lucifer* Yellow as a function of assays on cells in accordance with Example 2.

Concerning action of the formulas on the tight junctions of the cell layer, the apparent permeability of Lucifer Yellow was monitored for each assay (FIG. 7). Strong action of the microemulsions was observed and of the 10 and 25% Labrasol formulas on paracellular transport, of between 4 and $7 \cdot 10^{-6}$ cm/s. However, for the microemulsions this result can be related to membrane destabilisation. The 1 and 5% Labrasol formulations and 5% Gélucire® formulations also cause the transporting of Lucifer Yellow greater than $3 \cdot 10^{-7}$ cm/s. However it remains low since lower than $0.5 \times 10^{-6}$ cm/s (Table 4). The controls do not cause any opening of the tight junctions.

The MTS-PMS test showed that our formulas do not generate any cell toxicity.

Cell assays confirmed the low permeability of the baclofen with an apparent permeability lower than $3 \cdot 10^{-7}$ cm/s. This permeability is increased to $3 \cdot 10^{-6}$ cm/s for the Miglyol®/Labrasol® emulsion. It becomes very high for the Captex®/Capmul® and 25 and 10% Labrasol® emulsions ranging from 5 to $7 \cdot 10^{-6}$ cm/s. However, as for the results concerning Lucifer Yellow, the permeabilities associated with the microemulsions are certainly due to the observed loss of membrane integrity. The formulas of 1 and 5% Labrasol® and the formulas containing Gélucire® do not allow an increase in the apparent permeability of baclofen. The apparent permeability of metoprolol is very high since it is higher than $6 \cdot 10^{-6}$ cm/s, as expected. This was a control used for transcellular transport and its lack of effect shown above on the opening of the tight junctions validates the experimental conditions. Therefore the most promising formulas to increase through-membrane crossing of baclofen are the formulas containing Labrasol®, more particularly the 10% and 25% formulas which respectively allow 20 and 28-fold increases in the apparent permeability of nonformu-

TABLE 9

Particle Sizes of the Micro-Emulsions at 20° C. and at T = 14 D and T = 45 D

|  |  | Dilution | Dispersing medium | Proportion (%) | Size (nm) |
|---|---|---|---|---|---|
| Measurements at T = 14 days |||||| 
| non-diluted placebo emulsions | Emulsion Miglyol ®/Labrasol ® | N/A | Viscosity = 423 cP, Refractive index = 1.45 | No results | |
|  | Emulsion Captex ®/Capmul ® | N/A | Viscosity = 59 cP, Refractive index = 1.45 | 100 | 21.3 |
| non diluted emulsions with active ingredient | Emulsion Miglyol ®/Labrasol ® | N/A | Viscosity = 423 cP, Refractive index = 1.45 | No results | |
|  | Emulsion Captex ®/Capmul ® | N/A | Viscosity = 59 cP, Refractive index = 1.45 | 100 | 24.2 |
| Placebo emulsions after dilution | Emulsion Miglyol ®/Labrasol ® | 1/5000 | Water | 12-17<br>10-20<br>25-80<br>50-60 | 1<br>50-70<br>130-195<br>218-285 |
|  | Emulsion Captex ®/Capmul ® | 1/10000 | Water | 1-2<br>98-99 | 1-3<br>230-500 |
| Emulsions with active ingredient after dilution | Emulsion Captex ®/Capmul ® | 1/10000 | Water | 5<br>11-12<br>88 | 17<br>75-77<br>1000 |
|  | Emulsion Miglyol ®/Labrasol ® | 1/5000 | Water | 100 | 180-390 |
| Measurements at T = 45 days |||||| 
| Non-diluted emulsions with active ingredient | Emulsion Miglyol ®/Labrasol ® | N/A | Viscosity = 423 cP, Refractive index = 1.45 | No results | |
|  | Emulsion Captex ®/Capmul ® | N/A | Viscosity = 59 cP, Refractive index = 1.45 | 100 | 27.2 |
| Emulsions with active ingredient after dilution | Emulsion Miglyol ®/Labrasol ® | 1/5000 | Water | 12-13<br>14-20<br>65-87 | 1<br>70-74<br>190-200 |
|  | Emulsion Captex ®/Capmul ® | 1/10000 | Water | 1<br>99 | 4-5<br>530-630 |

TABLE 10

Particle Size of Water/Labrasol Mixtures at 20° C., at T = 7 D

| 25% Labrasol ® | 10% Labrasol ® | 5% Labrasol ® | 5% Labrasol ® Placebo | 1% Labrasol ® |
|---|---|---|---|---|
| 50% of 1 nm<br>50% of 15 nm | 50% of 1 nm<br>50% of 12 nm | 30% of 1 nm<br>40-50% of 10 nm<br>20-30% of 400 nm | 20% of 1 nm<br>80% of 13.5 nm | >2 μm |
|  | 10% Labrasol ® - 1/200<br>525.7 nm +/− 105.6; PI = 0.044 | 5% Labrasol ® - 1/100<br>657.5 nm +/− 170; PI = −0.091 |  |  |

Figure 8:
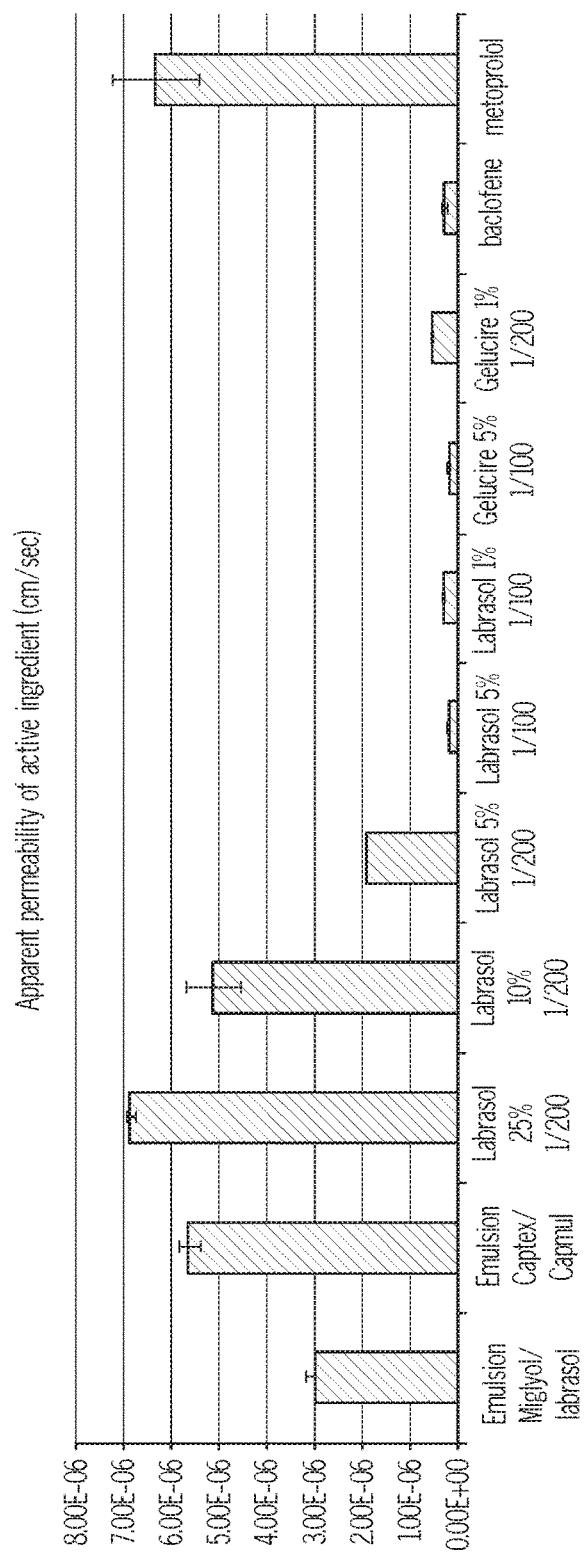
FIG. 8 is a graph depicting apparent permeability of active ingredient (baclofen or metoprolol) as a function of assays on cells in accordance with Example 2.

The apparent permeability results for baclofen in relation to the different formulas are given in FIG. 8.

lated baclofen. Also, the recovery rates calculated during assays were in the region of 100% which confirms the non degradation of the product during the assay. No loss was observed.

d. Solid Form Transport i. Granulation

Granulate containing 33% Labrasol® was obtained. It was of yellow colour and fatty to the touch.

Figure 9:
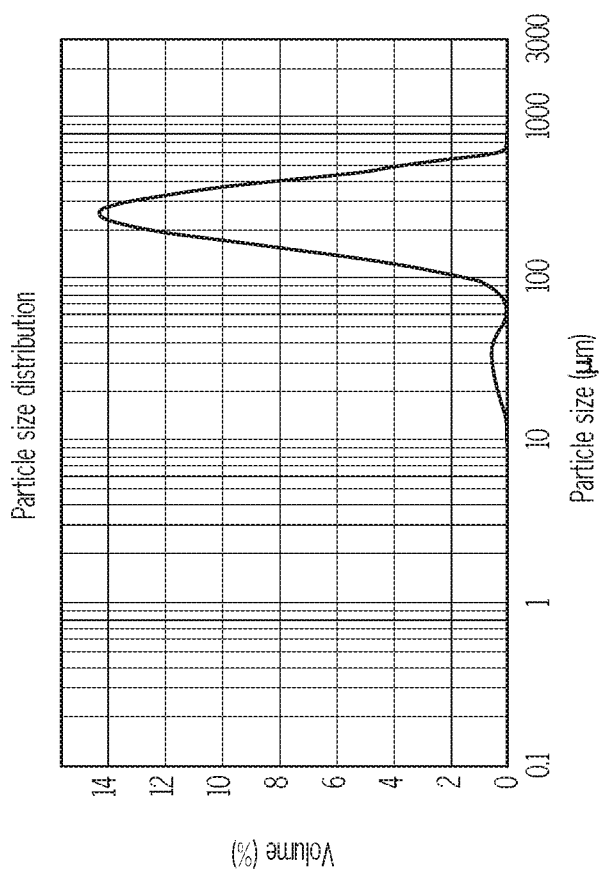
FIG. 9 is a graph of particle size distribution by volume of granulate composed of 33% Labrasol® in accordance with Example 2.

The particle size results are given in FIG. 9.

The data obtained with the Stav volumeter and the flow times are given in Table 11 below.

TABLE 11

Tapped volumes, densities, Carr index and flow time of granulate containing 33% Labrasol ®

| | Weight (g) | V0 (ml) | V10 (ml) | V500 (ml) | V1250 (ml) | ρ0 (g/ml) | tapped ρ (g/ml) | V10 − V500 (ml) | Carr index (100 × (V10 − V1250)/V10) | Flow time (s) |
|---|---|---|---|---|---|---|---|---|---|---|
| 33% Labrasol ® granulate | 100.14 | 184 | 172 | 158 | 158 | 0.54 | 0.63 | 14 | 8.14 | | ii. Adsorption

Adsorption assays on microcrystalline cellulose at the same concentration as obtained with granulation gave a yellow, fatty powder of "wet sand" appearance and forming clusters.

Adsorption tests on Neusilin® allowed a powder to be obtained containing 60% Labrasol®. This is a white mixture of dry appearance and highly volatile.

The objective of this step was to choose an excipient for future compression tests; the flow characteristics of the loaded excipients were determined by measuring flow rate and the Carr index (Ic) (Table 12).

TABLE 12

CHARACTERIZATION OF THE FLOW OF EXCIPIENTS LOADED AND NON-LOADED WITH LABRASOL ®

| | Flow rate (g/s) | Density (g/mL) | Ic (%) | Ic flowability |
|---|---|---|---|---|
| Avicel ® PH102 | 0 | 0.34 | 15.1 | Good |
| Avicel ® PH102 + Labrasol ® | 0 | 0.34 | 16.4 | Fairly good |
| Fujicalin ® | 20.2 | 0.47 | 6.9 | Excellent |
| Fujicalin ® + Labrasol ® | 19.3 | 0.65 | 9.5 | Excellent |
| Neusilin ® US2 | 2.9 | 0.15 | 8.9 | Excellent |
| Neusilin ® US2 + Labrasol ® | 23 | 0.48 | 6.0 | Excellent |
| Neusilin ® UFL2 | 0 | 0.11 | 25.0 | Acceptable |
| Neusilin ® UFL2 + Labrasol ® | 0 | 0.21 | 29.5 | Poor |
| Hubersorb ® 600 | 0 | 0.08 | 25.0 | Acceptable |
| Hubersorb ® 600 + Labrasol ® | 0 | 0.17 | 32.9 | Very poor |
| Syloïd ® 244FP | 0 | 0.07 | 14.8 | Good |
| Syloïd ® 244FP + Labrasol ® | 0 | 0.30 | 12.5 | Good |

Therefore the adsorbed powders without flow (Hubersorb® 600, Avicel® PH102, Neusilin® US2, Sylokl® 244FP) were not selected. Neusilin® US2 and Fujicalin® which were adsorbed exhibited very good flow and could therefore be used.

I. Discussion

Choice of Formulas for Permeability and Stability Assays

As expected, the solubility of the active ingredient in the liquid absorption enhancers proved to be very low since lower than 1 mg/ml. Baclofen is a hydrophilic active ingredient (AI) as indicated by its log P of −0.96 (Benet, et al., 2011), whereas the absorption enhancers are oils.

However, products such as Labrasol® and Gélucire® 50/13 have the particularity of having a high HLB in the order of 13-14 (Gattefossé) allowing their miscibility with water. The decision was therefore taken to form binary mixtures of Labrasol® or Gélucire® with an aqueous solution containing previously solubilised baclofen. The Labrasol®/water ratios were chosen to evaluate possible impact of Labrasol® concentration on the cells. Regarding Gélucire®, it was sought to maintain the mixture in liquid form at ambient temperature, which limited the range of concentration to below 5%. It was observed that at low concentrations (lower than 5% for Gélucire® and lower than 1% for Labrasol®) the mixtures of Labrasol and Gélucire exhibit turbidity. Particle size measurement indicates that the particles of the Labrasol® mixture are much larger than those observed in higher concentrations (2 μm versus 13 nm). The sizes obtained for the most concentrated solutions can account for the observed sedimentation. Finally, four formulas of Labrasol® at 1, 5, 10 and 25% and two formulas of Gélucire® at 1 and 5% were prepared and sent to the subcontractor.

As for the micro-emulsions composed of Miglyol®/Labrasol®, all three displayed visually clear, stable compositions (Table 13).

TABLE 13

STABLE MIGLYOL ®/LABRASOL ® MICRO-EMULSIONS

| Micro-emulsion | Miglyol ® | Labrasol ® | Tween ® 80 | Aqueous phase |
|---|---|---|---|---|
| 1 | 10% | 27% | 53% | 10% |
| 2 | 10% | 23% | 47% | 20% |
| 3 | 20% | 20% | 40% | 20% |

For assay on cells, composition 3 was selected on the basis of various criteria. First, the Tween® 80 used as surfactant is known to have toxicity problems; the formulas containing the least amount thereof would therefore appear to be safer. In addition, the proportion of water is higher and therefore allows the adding of a greater amount of active ingredient. Finally the proportion of Miglyol, of importance from an absorption enhancing viewpoint, is also higher.

The four microemulsions prepared from Captex®/Capmul® produced clear, stable formulas (Table 14).

TABLE 14

STABLE CAPTEX ®/CAPMUL ® MICROEMULSIONS

| Micro-emulsion | Captex ® | Capmul ® | Tween ® 80 | Aqueous phase |
|---|---|---|---|---|
| 1 | 60% | 20% | 10% | 10% |
| 2 | 64% | 22% | 11% | 3% |
| 3 | 55% | 28% | 14% | 3% |
| 4 | 56% | 26% | 13% | 5% |

On the basis of the same criteria as above, composition 1 was selected for assay on cells.

The permeability of baclofen could therefore be measured when incorporated in two microemulsions of different composition.

The transport mechanism of baclofen (Merino, et al., 1989) is active transport by means of transporters but these are saturated at high dose. Not knowing the transporter composition of the Caco-2 cells, it is sought to have a high concentration of baclofen in the formulas so that the transporters that are present are saturated. Therefore only the increase in paracellular transport was evaluated. The saturation concentration of baclofen in water is 3 mg/ml (internal pre-formulation report). However, its solubility is highly dependent on pH as indicated by the amine and carboxylic functions present on the molecule. Therefore the addition of 0.01 M fumaric acid shown to be compatible with baclofen by the internal pre-formulation report, allows the solubility of baclofen to be increased twofold to 6 mg/ml. The pH is then 3.88.

According to Constantinides et al (1996), the pH of a micro-emulsion does not influence its stability or its particle size if the surfactants used are neither ionised nor ionisable. Consequently the replacement of the aqueous phase of the micro-emulsions via 0.01 M fumaric acid up to 6 mg/ml of baclofen does not cause visual destabilisation of the microemulsions.

The stability of the systems was also monitored by particle size measurements 14 and 45 days after forming the microemulsions.

For the Captex®/Capmul® emulsion, a measurement of 21.3 nm was obtained at 14 days for the placebo formula, which confirms the presence of a microemulsion. A measurement of 24.2 nm was obtained for the formula with active ingredient indicating that the active ingredient does not have any influence on particle size as suggested in the work by (Prajapati, et al., 2012). However, work conducted by Buyukorturk et al (2010) and Gundogdu et al (2011) does show active ingredient influence on globule size. After 45 days the measured size was 27.2 nm, which confirms the stability of the system. To examine the influence of dilution on our sample, different dilutions were carried out. Throughout this study the systems became opaque indicating destabilisation of the formulas and possible phase inversion as explained by Prajapati et al. Phase inversion was confirmed by measurements on the Captex®/Capmul® emulsion since size measurements appeared to be much larger in the order of 230 to 500 nm. Here too the presence of the active ingredient does not appear to have an influence on these measurements.

Measurement of the particle size of the Miglyol®/Labrasol® emulsion could not be carried out on account of the high viscosity of the medium measured at 423 cP. To evaluate the stability of the Miglyol®/Labrasol® emulsion, the system was diluted on the assumption that dilution does not affect the particle size of an emulsion as reported by Prajapati et al. For the Miglyol®/Labrasol® emulsion, measurements taken with active ingredient at 14 days appeared to be higher than those obtained for the placebo. However, the measurements with active ingredient taken at 45 days were of the same order of magnitude as those of the placebo emulsion. It therefore seems difficult to draw a conclusion on the particle size stability of the Captex®/Capmul® emulsion. However it was nevertheless possible to observe the lack of any visual phase separation over the two-month observation period, which would indicate the macroscopic stability of the systems.

a. Interpretation of Permeability Results in Relation to Characterization of the Formulas The observed very low permeability of non-formulated baclofen, lower than $0.5 \times 10^{-6}$ cm/s, leads to the assumption that the applied concentration (30 µg/ml) is close to the saturation of the transporters. This value can be compared with the assays of 25% and 10% Labrasol® and 1% Gélucire® diluted in the same manner 200 times. 1% Gélucire® does not allow an increase in apparent permeability whilst the assays with Labrasol® allowed a strong increase of this permeability 20- and 28-fold.

Regarding the formulas diluted 100 times (5% Labrasol®, 1% Labrasol® and 5% Gélucire®), the permeability values were very low; at times lower than that of nonformulated baclofen. Yet the concentrations of baclofen deposited on the cells for these assays were twice higher than those of the negative control. It is therefore possible that the concentration of the control does not fully lie at complete saturation of the transporters. In this case the permeability values cannot be properly compared since they are dependent on the concentration of active ingredient which proves to differ from one formula to another. The assays with Gélucire® are a good illustration thereof. The Gélucire® concentration was higher for 5% Gélucire® than for 1% Gélucire®, even after dilution. This could account for the permeability results with Lucifer Yellow which were higher in the former case and would seem to indicate a slight effect of Gélucire on paracellular transport. However, the permeability of baclofen was higher with 1% Gélucire®, no doubt due to the lower concentration of baclofen allowing facilitated transport of the molecule.

Despite the effect of baclofen concentration, a strong difference in permeability can nevertheless be observed between the 10 and 25% Labrasol® formulas and the 1 and 5% Labrasol® formulas. Initially, it was sought to find structural differences of the mixtures by measuring particle size. Koga et al demonstrated the importance of Labrasol® concentration on particle size which appeared to increase with concentration. Baclofen would therefore be better surrounded by Labrasol® allowing an increase in its permeability since the active ingredient and the lipid component allowing the opening of the tight junctions possibly arrive at the same time at the membrane. Initial measurements on the nondiluted formulas were performed. For the 1 to 5, 10 and 25% formulas, the measurements obtained were of the same order of magnitude as those measured by Koga et al. but no relationship between Labrasol® concentration and particle size was clearly identified. The onset of a 400 nm population was even observed for the 5% formula which disappeared in the placebo formula and would indicate influence of the active ingredient on particle size. However, measurements performed on the formulas after dilution cancel out the hypothesis of influence of particle size since the observed differences disappear. In addition a significant increase in particle size was noted with dilution.

It is pointed out that taking into account the dilutions performed on the cells, two identical concentrations of Labrasol® were assayed (Table 15) and did not give the same permeability results. This point is an argument in favour of the importance of the initial concentration of active ingredient regarding increased membrane transport. The active ingredient/Labrasol® ratio therefore proves to be of importance in the observed results. Table 15 gives the increase factors observed in relation to the active ingredient/Labrasol® ratios used.

TABLE 15

Increase In baclofen permeability as a function of active ingredient /LabrasoL ® ratio and Labrasol ® concentration

| AI/Labrasol ® ratio | Papp increase factor | Labrasol ® concentration |
| --- | --- | --- |
| 1/1.7 | 0 | 0.01% |
| 1/8.8 | 0 | 0.05% |
| 1/13.4 | 7 | 0.03% |
| 1/18.5 | 20 | 0.05% |
| 1/55.5 | 28 | 0.125% |

It would therefore appear that the increase in apparent permeability of baclofen only occurs on and after a certain Labrasol® threshold in relation to baclofen concentration.

An increase in apparent permeability was also obtained for the micro-emulsions However, despite this observation these were not taken into account due to the toxicity evidenced on the cell layer through loss of membrane integrity.

Finally, having regard to the significant increase in permeability obtained with Labrasol®, the remainder of the study chiefly focuses on this excipient in particular for assays of pharmaceutical forms.

b. Adsorption/Granulation Assays

Transport assays of the solid form obtained by granulation with microcrystalline cellulose did not allow the adding of an amount of Labrasol® higher than 33%. By visual comparison with the adsorption assay the Labrasol® granulate appeared to exhibit improved properties via a less "moist" effect, with the obtaining of a granulate which in theory would allow better flow properties in particular for future compression assays. The Carr index calculated at 8.14 led to assuming good flow properties but low compressibility properties. However with a standardized funnel no flow was observed.

Other adsorption assays were then performed on Neusilin®, a silicate having adsorption capacity three times higher than microcrystalline cellulose (Neusilin application data, www.Neusilin.com). The adsorption technique is preferred since it allows the adding of larger quantities of liquid compared with granulation. This latter technique also requires the adsorption of a certain amount of water which reduces the volume available for the oil. A dry mixture containing 60% Labrasol® was obtained which is encouraging and can allow the use of this powder in an oral pharmaceutical form.

LIST OF ABBREVIATIONS

| | |
| --- | --- |
| Ac | Acid |
| ATP | Adenosine triphosphate |
| BCS | Biopharmaceutical Classification System |
| BP | British Pharmacopoeia |
| BSA | Bovine serum albumin |
| C10, C8 | Fatty acid composed of 10 or 8 carbon atoms |
| cP | centiPoise |
| $d_{10}$, $d_{50}$, $d_{90}$ | 10, 50 and 90% deciles |
| DAG | Diacylglycerol |
| DMEM | Dulbecco's Modified Eagle Medium |
| DMF | Drug master File |
| DSC | Differential scanning calorimetry |
| W/O | Water-in-oil |
| EMEA | European Agency for the Evaluation of Medicinal Products |
| EP | European Pharmacopoeia |
| FDA | Food and Drug Administration |
| GRAS | Generally Recognized As Safe |
| O/W | Oil-in-water |
| HBSS | Hank's Balanced Salt Solution |
| HEPES | 4-(2-hydroxyethyl)-1-piperazine ethane sulfonic acid |
| HLB | Hydrophilic/Lipophilic Balance |
| PI | Polydispersity Index |
| IP3 | Inositol triphosphate |
| TJ | Tight Junctions |
| LC/MS/MS | Liquid chromatography coupled with tandem mass spectrophotometry |
| LY | Lucifer yellow |
| ME | Microemulsion |
| MTT | 3-(4,5-dimethylthiazol-2-yl)-2,5-diphenyl tetrazolium bromide |
| unkn. | Unknown |
| NF | French standard |
| WHO | World Health Organization |
| AI | Active ingredient |
| $P_{app}$ | Apparent permeability |
| P-gp | P-glycoprotein |
| PIP2 | phosphatidylinositol 4,5-bisphosphate |
| PLC | Phospholipase C |
| rpm | Revolutions per minute |
| t or T | Time |
| T5, T65, T125 | Time at 5, 65 or 125 minutes |
| $T_{amb}$ | Ambient temperature |
| TEER | Transepithelial electrical resistance |
| m.p. | Melting point |
| USP | United States Pharmacopoeia |
| $V_0$ | Bulk volume |
| V10, V500, V1250 | Apparent volume after 10, 500 or 1250 taps |
| ZO | Zonula occludens |
| ρ | Density |

BIBLIOGRAPHY

Abitec Fiches techniques//Capmul MCM EP; Captex 355 EP/NF; Captex 300 EP/NF; Captex 200P.—2012.

Anilkumar P [et al.] A rationalized description on study of intestinal barrier, drug permeability and permeation enhancers [Revue]//Journal of Global Trends in Pharmaceutical Sciences vol 2, n° 4.—2001.—pp. 431-449.

Boonme P [et al.] Characterization of micro-emulsion structures in the pseudoternary phase diagram of isopropyl palmitate/water/brij 97:1-butanol [Article]//AAPS PharmSciTech, vol 6, n° 2, article 45.—2006.

Brochette Pascal Emulsification-Elaboration et études des émulsions, J 2150 [En ligne]//Techniques de l'ingénieur.—2012.—22 Mar. 2012.

Buyukorturk F, Benneya J, C et Carrier R, L Impact of emulsion-based drug delivery systems on intestinal permeability and drug release kinetics [Article]//Journal of Controlled Release, vol 142.—2010.—pp. 22-30.

Cho S-W, Lee J, S et Choi S-H Enhanced oral bioavailability of poorly absorbed drug. I. Screening absoption carrier for the ceftriaxone complex [Revue]//Journal of Pharmaceutical Sciences, vol 96, n°3.—2004.—pp. 612-620.

Choi S-H, Lee J-S et Keith D Compositions and methods to improve the oral absorption of antimicrobial agents [Brevet]: EP 1 294 361 B1—WO 2001/097851.—International, 2011.

Constantinides P, P [et al.] Water-in-oil microemulsions containing medium-chain fatty acids/sats: formulation and intestinal absorption enhancement evaluation [Revue]//Pharmaceutical Research, vol 13, n°2.—1996.—pp. 210-215.

Constantinides P, P et Scalart J-P Formulation and physical characterization of water-in-oil micro-emulsions containing long-versus medium-chain glycerides, [Revue]//International Journal of Pharmaceutics, vol 158.—1997.—pp. 57-68.

Constantinides P, P Lipid micro-emulsions for improving drug dissolution and oral absorption: Physical and biopharmaceutical aspects [Revue]//Pharmaceutical Research, vol 12, n°11.—1995.—pp. 1561-1572.

Dahan A, Miller J, M et Amidon G, L Prediction of solubility and permeability class membership: provisional BCS Classification of the world's top oral drug [Revue]//The AAPS Journal, vol 11, n°4.—2009.—pp. 740-746.

Davis S, S Formulation strategies for absorption windows [Revue]//Drug Discovery today, vol 10, n°4.—2005.

DeLuca T, Kaszuba M et Mattison K Optimizing silicone emulsion stability using zeta potential [Article]//American Laboratory News.—Juillet 2006.

Fan Y [et al.] Improved intestinal delivery of salmon calcitonin by water-in-oil micro-emulsions [Revue]//International Journal of Pharmaceutics, vol 416.—2011.—pp. 323-330.

Fasinu P [et al.] Diverse approaches for the enhancement of oral drug bioavailability [Revue]//Biopharmaceutics and drug disposition, vol 32.—2011.—pp. 185-209.

FDA Code of federal regulations title 21, part 172 and 184 [En ligne]//U.S. Food and Drug Administration.—1 Apr. 2011-9 May 2012.—http:/www.accessdata.fda.gov.

Gattefossé Lipid excipients for oral bioavailability enhancement.

Gundogdu E, Gonzales Alvarez I et Karasulu E Improvement of effect of water-in-oil microemulsion as an oral delivery system for fexofenadine: in vitro and in vivo studies [Article]//International Journal of Nanomedicine, vol 6.—2011.—pp. 1631-1640.

ICI Americas Inc The HLB system: a timesaving guide to emulsifier selection [Livre].—Wilmington: Chemmunique, 1976.

Jannin V, Musakhanian J et Marchaud D Approaches for the development of solid and semi-solid lipid-based formulations [Article]//Advanced drug delivery reviews, vol 60.—2008.—pp. 734-746.

Koga K, Kawashima S et Murakami M In vitro and in situ evidence for the contribution of labrasol and Gelucire 44/14 on transport of cephalexine and cefoperazone by rat intestine [Revue]//European Journal of Pharmaceutics and biopharmaceutics, vol 54.—2002.—pp. 311-318.

Leisen C, C [et al.] Lipophilicities of baclofen ester prodrugs correlate with affinities to the ATP-dependant efflux pump P-glycoprotein: relevance for their permeation across the blood-brain barrier? [Revue]//Pharmaceutical Research, vol 20, n°5.—2003.—pp. 772-778.

Lin Y [et al.] Effects of Labrasol and other pharmaceutical excipients on the intestinal transport and absorption of rhodamin123, a P-Glycoprotein substrate, in rats [Revue]//Biological and Pharmaceutical Bulletin, vol 30, n°7.—2007.—pp. 1301-1307.

Maher S [et al.] Safety and efficacy of sodium caprate in promoting oral drug absorption: from in vitro to the clinic [Revue]//Advanced Drug Delivery Reviews, vol 31.—2009.—pp. 1427-1449.

Merino M [et al.] Evidence of a specialized transport mechanism for the intestinal absorption of baclofen [Revue]//Biopharmaceutics and Dreug disposition, vol 10.—1989.—pp. 279-297.

Motlekar N [et al.] Oral delivery of low-molecular-weight heparin using sodium caprate as absorption enhancer reaches therapeutic levels [Revue]//Journal of drug targeting, vol 13, n°10.—2005.—pp. 573-583.

Nataf S Le tissu épithélial [En ligne]//Histologie.—11 May 2012.—http://histoblog.viabloga.com.

Nekkanti V [et al.] Solid self-microemulsifying formulation for candesartan cilexetil [Revue]//AAPS PharmSciTech, vol 11, n°1.—2010.—pp. 9-17.

Nollevaux G [et al.] Development of a serum-free co-culture of human intestinal epithelium cell-lines (Caco-2/HT29-5M21) [Article]//BMC cell Biology, vol 7, n°20.—2006.—pp. 1471-2121.

Oroxcell Protocole d'essais sur cellules Caco-2.—Romainville: [s.n.], 15 Dec. 2011.

Pontier Catherine Coculture de cellules Caco-2/TC7 HT29MTX: comparaison avec les modèles Caco-2/TC7 et HT 29MTX [Rapport].—[s.l.]: Université de Paris XI, centre d'études pharmaceutiques, 1997-1998.

Prajapati H, N, Dalrymple D, M et Serajuddin A, T, M A comparative evaluation of Mono- Di- and Triglyceride of medium chain fatty acids by lipid/surfactant/water phase diagram, solubility determination and dispersion testing for application in pharmaceutical dosage form development [Article]//Pharmaceutical research, vol 29.—2012.—pp. 285-305.

pubchem Sodium Caprate [En ligne]//pubchem.—10 Apr. 2012.—http://pubchem.ncbi.nlm.nih.gov.

Redzic Z Molecular biology of the blood-brain and the blood-cerebrospinal fluid barriers: similarities and differences [Article]//Fluids and barriers of the CNS, vol 8, n°3.—2011.

Sachs-Barrable S [et al.] Lipid excipients peceol and gelucire 44/14 decrease P-glycoprotein mediated efflux of rhodamine 123 partially due to modifying P-glycoprotein protein expression within Caco-2 cells [Revue]//Journal of Pharmacy and Pharmaceutical Sciences, vol 10, n°3.—2007.—pp. 319-331.

Sasol Germany GmbH Product information 09.04//Miglyol 812, 812, 818, 829, 840 neutral oils for pharmaceutical and cosmetics.—2012.

Sha X [et al.] Effect of self-microemulsifying drug delivery systems containing labrasol on tight junctions in Caco-2 cells [Revue]//European Journal of Pharmaceutical Sciences, vol 24.—2005.—pp. 477-486.

Sigentec Tests de cytotoxicité [En ligne]//site Web Sigentec.—7 May 2012.—http://www.sigentec.com/html/fr/tests/cytotoxicite.html.

Benet L, Z, Broccatelli F et Oprea T, I BDDCS applied to ver 900 drugs [Article]//The AAPS Journal.—2011.

Kochak G, M [et al.] The pharmacokinetics of baclofen derived from intestinal infusion [Article]//Clin Pharmacol Ther.—1985.—Vol. 38: pp 251-257.

K Merino M [et al.] Evidence of a specialized transport mechanism for the intestinal absorption of baclofen [Revue]//Biopharmaceutics and Drug disposition, vol. 10.—1989.—pp. 279-297.

Neusilin Application data [On line]//Neusilin.com.—http://www.neusilin.com/library/application_data.—May 6, 2012.

European Pharmacopoeia 7th Edition//Chapters 2.09.34—Bulk density and Tapped Density & 2.09.36—Powder flow.—2012.—Vol. 7.4.

The invention claimed is:

1. An oral pharmaceutical formulation in tablet form consisting of:
   a neutral carrier impregnated with an oil-in-water microemulsion, dried and compressed with compression excipients,
   said oil-in-water microemulsion being between an aqueous solution comprising water and baclofen and an oil phase comprising an oil excipient self-emulsifiable in contact with water, said oil excipient self-emulsifiable in contact with water being a mixture of mono-, bi- and triglycerides of PEG-8 esterified fatty acids in the proportion of 50 to 80% caprylic acid and 20 to 50% capric acid, said oil-in-water microemulsion comprising from 2 to 30% oil phase and from 70% to 98% aqueous solution, based on the total weight of the oil-in-water microemulsion;

wherein said tablet form contains residual moisture of less than 5%.

2. The formulation according to claim 1, said oil excipient self-emulsifiable in contact with water having an HLB value higher than 12.

3. The formulation according to claim 1, wherein said oil phase represents 5 to 25% of the oil-in-water microemulsion.

4. The formulation according to claim 1, said oil excipient self-emulsifiable in contact with water being contained in a ratio of 1:10 to 1:100 by weight relative to baclofen.

5. A method of treatment of alcohol dependence or for the maintaining of alcohol abstinence, comprising administration of the formulation according to claim 1 to a patient in need.

* * * * *